(12) United States Patent
Van Der Schaaf et al.

(10) Patent No.: US 6,696,479 B2
(45) Date of Patent: Feb. 24, 2004

(54) CRYSTALLINE FORMS

(75) Inventors: Paul Adriaan Van Der Schaaf, Allschwil (CH); Claudia Marcolli, Zürich (CH); Martin Szelagiewicz, Münchenstein (CH); Andreas Burkhard, Basel (CH); Heinz Wolleb, Fehren (CH); Annemarie Wolleb, Fehren (CH)

(73) Assignee: Ciba Specialty Chemicals Corporation, Tarrytown, NY (US)

( * ) Notice: Subject to any disclaimer, the term of this patent is extended or adjusted under 35 U.S.C. 154(b) by 0 days.

(21) Appl. No.: 10/208,687

(22) Filed: Jul. 30, 2002

(65) Prior Publication Data

US 2003/0032666 A1 Feb. 13, 2003

(30) Foreign Application Priority Data

Aug. 3, 2001 (EP) .............................................. 01810756

(51) Int. Cl.$^7$ .................... A61K 31/405; C07D 209/12; C07D 209/24; A61P 43/00
(52) U.S. Cl. ........................ 514/410; 514/412; 514/415; 514/419; 514/951; 424/400; 424/489; 548/491; 378/70
(58) Field of Search ................................. 514/410, 419, 514/412, 415, 951; 548/491; 378/70; 424/400, 489

(56) References Cited

U.S. PATENT DOCUMENTS 4,739,073 A    4/1988    Kathawala .................. 548/406

FOREIGN PATENT DOCUMENTS

| WO | 97/49681 | 12/1997 |
| WO | 02/36563 | 5/2002 |

OTHER PUBLICATIONS

O. Tempkin et al., Tetrahedron, vol. 53, No. 31, pp. 10659–10670 (1997).

Primary Examiner—Frederick Krass
Assistant Examiner—Clinton Ostrup
(74) Attorney, Agent, or Firm—Kevin T. Mansfield

(57) ABSTRACT

Novel crystalline forms of Fluvastatin sodium hydrates were found, referred to hereinafter as polymorphic Forms C, D, E and F. Furthermore, the present invention is directed to processes for the preparation of these crystalline forms, a process for the preparation of highly crystalline Fluvastatin sodium Form A, and pharmaceutical compositions comprising the crystalline forms.

17 Claims, 6 Drawing Sheets

CRYSTALLINE FORMS

The present invention is directed to novel crystalline forms of Fluvastatin sodium, processes for their preparation and pharmaceutical compositions comprising these crystalline forms.

Fluvastatin sodium is known by its chemical name (±)-7-(3-(4-fluorophenyl)-1-(1-methylethyl)-1H-indol-2-yl)-3,5-dihydroxy-6-heptenoic acid monosodium salt. Fluvastatin sodium is a racemic mixture of the 3R,5S- and 3S,5R-dihydroxy enantiomers and has the following formula:

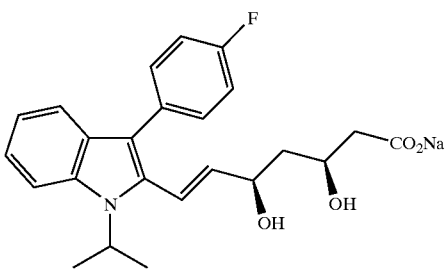

Fluvastatin sodium is an inhibitor of 3-hydroxy-3-methylglutaryl coenzyme A (HMG-CoA) and is used to lower the blood cholesterol level.

Fluvastatin as well its sodium salt are disclosed in U.S. Pat. No. 4,739,073. In this patent Fluvastatin sodium is obtained by lyophilization. WO-A-97/49681 and its US equivalent U.S. Pat. No. 6,124,340 describe that lyophilization of Fluvastatin sodium yields a mixture of a crystalline form, designated as Form A, and amorphous material, and disclose a new crystalline form, designated as Form B. The estimated amount of form A obtained by lyophilization as described in these patents is about 50%. The crystalline Form B is obtained either by transformation of material containing Form A in a slurry of a mixture of an organic solvent and water, or by crystallization from an organic solvent and water mixture. It is also described that form B is less hygroscopic than Form A or the amorphous form of Fluvastatin sodium which improves handling and storage of the compound. However, there is still a need for new crystalline forms which are less hygroscopic than Form A and which can be obtained from aqueous solutions.

We have now surprisingly found that Fluvastatin sodium can be prepared as novel crystalline hydrates which have improved stability and are obtained from aqueous solutions without the risk of residual organic solvent. These novel crystalline hydrates, herein designated as Form C, D, E and F, are less susceptible towards air humidity, and show high stability and are easier to handle at normal environmental humidity levels. The novel crystalline forms of Fluvastatin sodium are novel hydrates with water contents ranging from 3 to 32%. In addition we found a new process for the preparation of highly crystalline Fluvastatin sodium Form A. Thus the present invention provides the following novel crystalline forms of Fluvastatin sodium:

A crystalline polymorph of (±)-7-(3-(4-fluorophenyl)-1-(1-methylethyl)-1H-indol-2-yl)-3,5-dihydroxy-6-heptenoic acid monosodium salt which exhibits a characteristic X-ray powder diffraction pattern with characteristic peaks expressed in d-values (Å):

23.8 (vs), 11.8 (w), 7.8 (vs), 7.6 (vw), 7.4 (vw), 6.4 (vw), 6.1 (vw), 5.90 (w), 5.00 (vw), 4.88 (w), 4.73 (m), 4.56 (w), 4.40 (vw), 4.12 (vw), 4.03 (vw), 3.96 (vw), 3.50 (vw), 3.36 (vw), 2.93 (vw), herein designated as Form C. Here and in the following the abbreviations in brackets mean: (vs)=very strong intensity; (s)=strong intensity; (m)=medium intensity; (w)=weak intensity; and (vw)=very weak intensity. A characterisitic X-ray powder diffraction pattern for Form C is depicted in FIG. 2.

A crystalline polymorph of (±)-7-(3-(4-fluorophenyl)-1-(1-methylethyl)-1H-indol-2-yl)-3,5-dihydroxy-6-heptenoic acid monosodium salt which exhibits a characteristic X-ray powder diffraction pattern with characteristic peaks expressed in d-values (Å):

24.6 (vs), 12.5 (w), 8.3 (vs), 7.4 (vw), 6.2 (m), 4.97 (w), 4.85 (vw), 4.52 (vw), 4.40 (vw), 4.14 (vw), 3.96 (vw), 3.41 (vw), 3.10 (vw), herein designated as Form D. A characteristic X-ray powder diffraction pattern for Form D is depicted in FIG. 3.

A crystalline polymorph of (±)-7-(3-(4-fluorophenyl)-1-(1-methylethyl)-1H-indol-2-yl)-3,5-dihydroxy-6-heptenoic acid monosodium salt which exhibits a characteristic X-ray powder diffraction pattern with characteristic peaks expressed in d-values (Å):

27.6 (m), 13.9 (vw), 9.2 (m), 8.5 (vw), 8.1 (vw), 7.4 (vw), 6.9 (s), 6.1 (vw), 4.98 (m), 4.77 (m), 4.63 (m), 4.15 (w), 4.03 (w), 3.97 (vw), 3.52 (vw), 3.33 (vw), 3.08 (vw), 2.99 (vw), herein designated as Form E. A characteristic X-ray powder diffraction pattern for Form E is depicted in FIG. 4.

A crystalline polymorph of (±)-7-(3-(4-fluorophenyl)-1-(1-methylethyl)-1H-indol-2-yl)-3,5-dihydroxy-6-heptenoic acid monosodium salt which exhibits a characteristic X-ray powder diffraction pattern with characteristic peaks expressed in d-values (Å):

29.6 (w), 14.8 (vw), 9.9 (w), 8.6 (vw), 8.3 (vw), 7.4 (s), 6.6 (vw), 6.2 (vw), 5.93 (w), 5.03 (m), 4.94 (m), 4.35 (vw), 4.23 (w), 3.98 (vw), 3.54 (vw), 2.98 (vw), herein designated as Form F. A characteristic X-ray powder diffraction pattern for Form F is depicted in FIG. 5.

Furthermore, the present invention is directed to processes for the preparation of Form C, D, E, F and highly crystalline Form A.

Forms C, D, E and F can be prepared according to a process, wherein Fluvastatin sodium is exposed to an atmosphere having a defined relative humidity.

Form C of Fluvastatin sodium can generally be prepared from either the crystalline Forms A, D, E, F or amorphous Fluvastatin sodium, or mixtures thereof, for example by equilibration under relative humidity conditions from about 15 to 25% (for example for 6 to 24 hours). As a rule the estimated water content can range from 3–6%.

Form D of Fluvastatin sodium can generally be prepared from either the crystalline Forms A, C, E, F or amorphous Fluvastatin sodium, or mixtures thereof, for example by equilibration under relative humidity conditions from about 30 to 50% (for example for 6 to 24 hours). As a rule the estimated water content can range from 6–12%.

Form E of Fluvastatin sodium can generally be prepared from either the crystalline Form A, C, D, F or amorphous Fluvastatin sodium, or mixtures thereof, for example by equilibration under relative humidity conditions from about 55 to 75% (for example for several days). As a rule the estimated water content can range from 15–22%.

Form F of Fluvastatin sodium can generally be prepared from either the crystalline Form A, C, D, E or amorphous Fluvastatin sodium, or mixtures thereof, for example by equilibration under relative humidity conditions from about 80 to 90% (for example for several days). As a rule the estimated water content can range from 24–32%.

Highly crystalline Fluvastatin sodium Form A can generally be prepared by equilibration of an aqueous suspension or solution of Fluvastatin sodium for several hours at temperatures from about 0 to 10° C. and subsequent drying by lyophilization. The process can be accelerated by additional seeding with crystals of Form A during the equilibration period. A characteristic X-ray powder diffraction pattern for highly crystalline Form A is depicted in FIG. 1. The crystallinity of this material is estimated by the powder diffraction spectrum to be more than 90%. The estimated water content is below 2%.

A preferred process for the preparation of highly crystalline Fluvastatin sodium Form A comprises treating an aqueous solution of (±)-7-(3-(4-fluorophenyl)-1-(1-methylethyl)-1H-indol-2-yl)-3,5-dihydroxy-6-heptenoic acid monosodium salt in order to effect at least minimal precipitation of the compound, followed by freeze drying.

It is preferred that the aqueous solution is cooled and subsequently the suspension is freeze dried. As to this embodiment it is preferred that the aqueous solution is prepared at a temperature of 20 to 80° C., especially 30 to 80° C., and is cooled to a temperature of 0 to 15° C. in order to effect precipitation of the compound.

Advantagously seeding crystals of Form A can be added.

Small changes in the relative air humidity can cause small deviations in the d-values of characteritic peaks in the X-ray powder diffraction patterns. For example, crystalline Fluvastatin sodium Form D prepared under a relative humidity of 35% exhibits characteristic X-ray powder diffraction peaks in d-values (Å) at 24.6 (vs), 12.5 (w), 8.3 (vs) and 6.2 (m), whereas a sample prepared under a relative humidity of 50% exhibits characteristic X-ray powder diffraction peaks in d-values (Å) at 26.2 (vs), 13.2 (w), 8.9 (vs) and 6.7 (m), see FIG. 6.

Therefore, the present invention is also directed to a crystalline polymorph of (±)-7-(3-(4-fluorophenyl)-1-(1-methylethyl)-1H-indol-2-yl)-3,5-dihydroxy-6-heptenoic acid monosodium salt which can have small deviation in the characteristic peaks expressed in d-values (Å) in the X-ray powder diffraction pattern in the range of 24.6–26.2 (vs), 12.5–13.2 (w), 8.3–8.9 (vs) and 6.2–6.7 (m) depending on a relative humidity ranging from 35 to 50%, wherein (vs)= very strong intensity; (m)=medium intensity; (w)=weak intensity.

Another object of the present invention are pharmaceutical compositions comprising an effective amount of crystalline polymorphic Form C, D, E or F, and a pharmaceutically acceptable carrier. Another subject of the present invention are pharmaceutical compositions comprising an effective amount of highly crystalline polymorphic Form A, and a pharmaceutically acceptable carrier.

The polymorphic forms may be used as single components or mixtures.

As to pharmaceutical compositions of Fluvastatin sodium it is preferred that these contain 25–100% by weight, especially 50–100% by weight, of at least one of the novel forms, based on the total amount of Fluvastatin sodium. Preferably, such an amount of the novel polymorphic forms of Fluvastatin sodium is 75–100% by weight, especially 90–100% by weight. Highly preferred is an amount of 95–100% by weight.

The following Examples illustrate the invention in more detail. Temperatures are given in degrees Celsius.

EXAMPLE 1
Preparation of Highly Crystalline Polymorphic Form A

A 30 ml aqueous solution of 30° C. containing ca. 3 grams of Fluvastatin sodium was cooled to about 2° C. and was allowed to stand at this temperature for 6 hours. Subsequently, the off-white coloured suspension was frozen using a dry-ice bath and dried by lyophilization for 24 hours. A Karl Fisher titration revealed a water content below 2%. From its X-ray powder diffraction pattern it was estimated that the crystallinity is more than 90%, see FIG. 1.

EXAMPLE 2
Preparation of Polymorphic Form C

A 100 mg sample of Fluvastatin sodium A was equilibrated in an X-ray diffractometer under relative humidity conditions of about 20% for 12 hours. This relative humidity was sufficient to initiate the crystallization of Form C, see FIG. 2.

EXAMPLE 3
Preparation of Polymorphic Form D

A 5 gram sample of Fluvastatin sodium, obtained by lyophilization, was stored over a saturated solution of $MgCl_2$ $6H_2O$ at ambient temperature, i.e. under an humidity of approximately 33% for about 12 hours. The obtained sample is crystalline and corresponds to Fluvastatin sodium Form D, see FIG. 3.

EXAMPLE 4
Preparation of Polymorphic Form E

A 100 mg sample of Fluvastatin sodium A was equilibrated in an X-ray diffractometer under relative humidity conditions of about 65%. This relative humidity was sufficient to initiate the crystallization of Form E, see FIG. 4.

EXAMPLE 5
Preparation of Polymorphic Form F

A 100 mg sample of Fluvastatin sodium A was equilibrated in an X-ray diffractometer under relative humidity conditions of about 85%. This relative humidity was sufficient to initiate the crystallization of Form F, see FIG. 5.

EXAMPLE 6

A mixture of 0.5 gram of Fluvastatin sodium Form A and 0.5 gram of Fluvastatin sodium Form D were merged in a mortar under normal environmental humidity conditions giving a homogeneous off-white powder. A X-ray powder diffraction measurement showed the substance to be crystallographically pure Fluvastatin sodium Form D.

Figure 1:
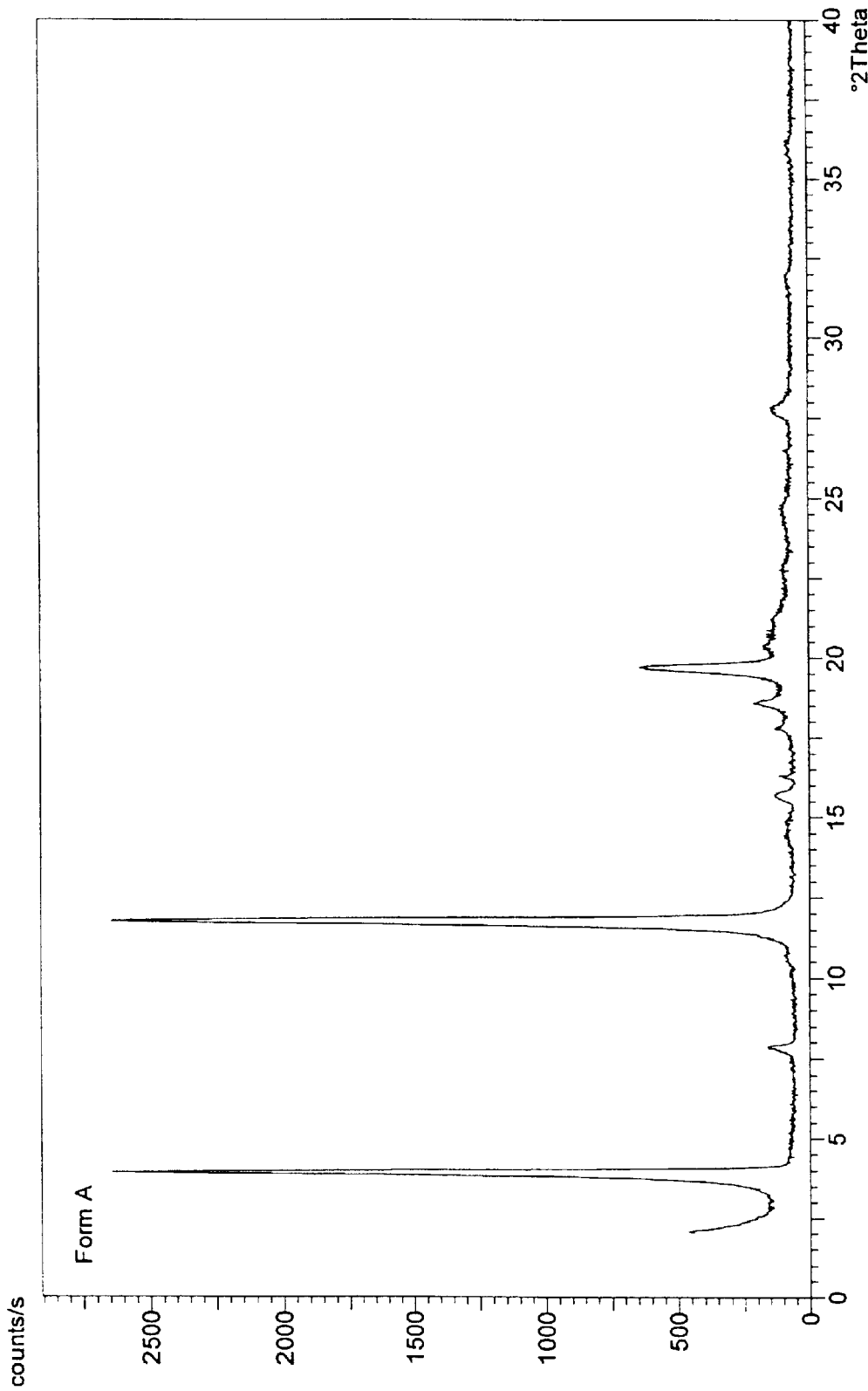
FIG. 1 is a characteristic X-ray powder diffraction pattern for highly crytalline Form A.
Figure 2:
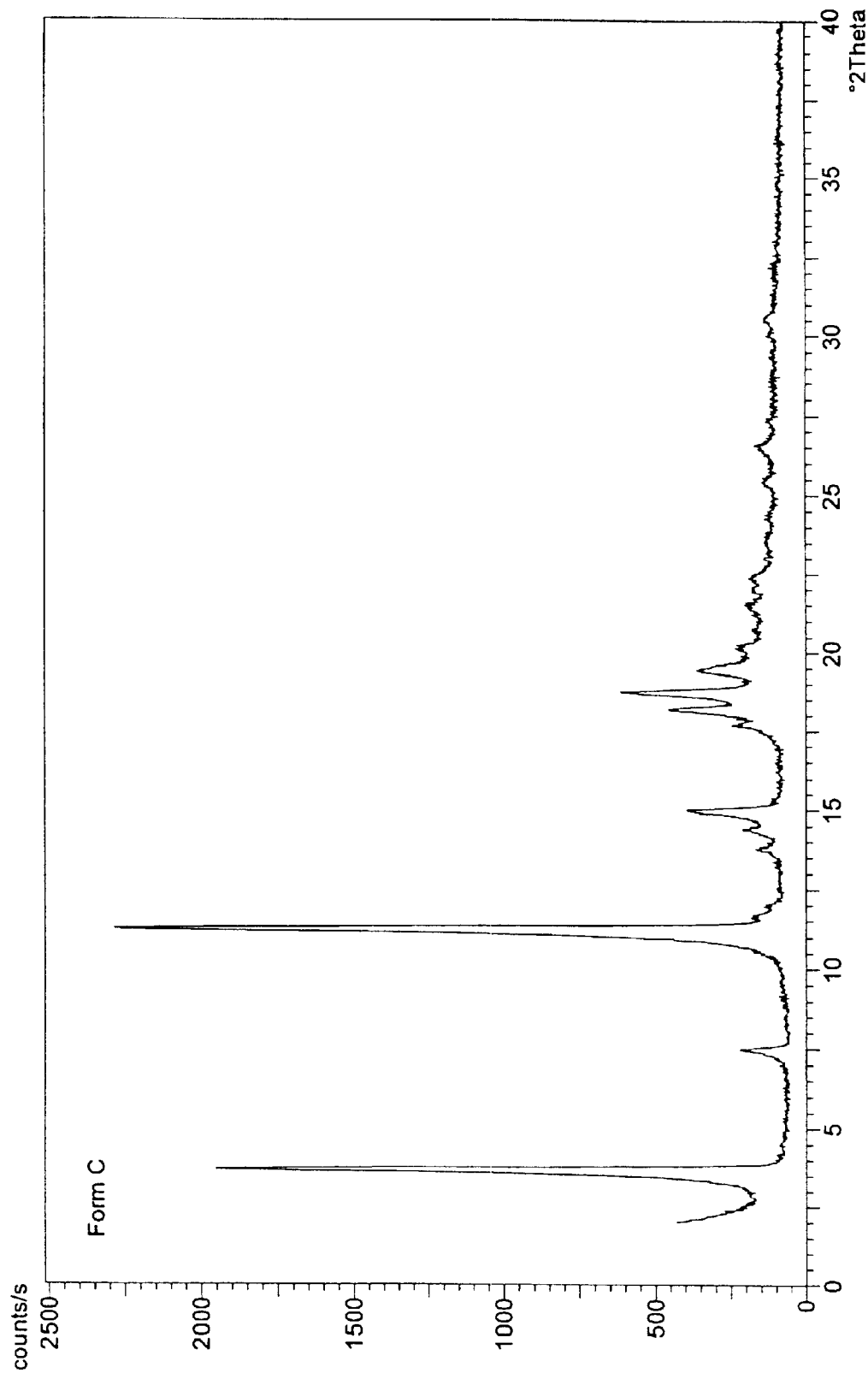
FIG. 2 is a characteristic X-ray powder diffraction pattern for Form C.
Figure 3:
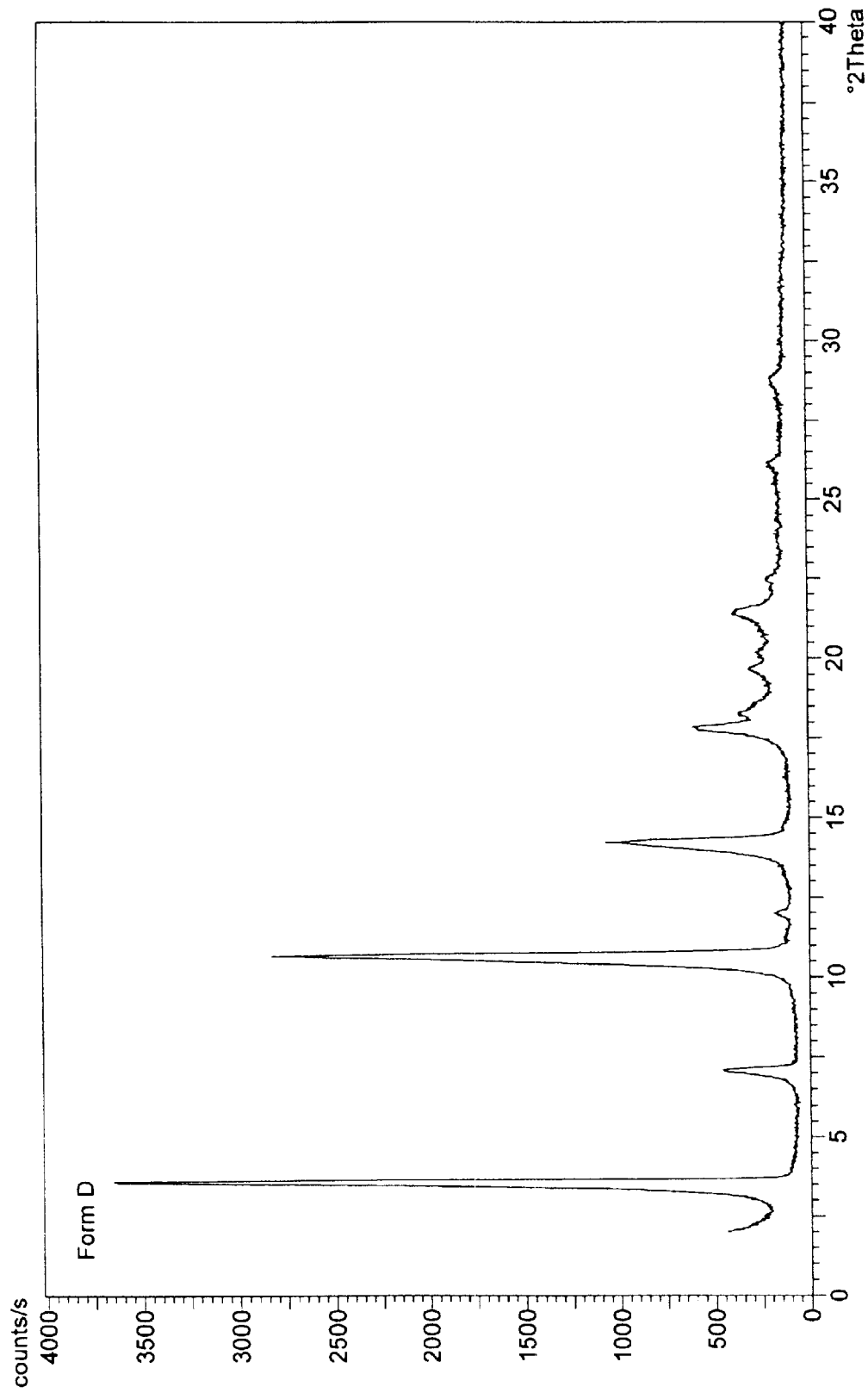
FIG. 3 is a characteristic X-ray powder diffraction pattern for Form D.
Figure 4:
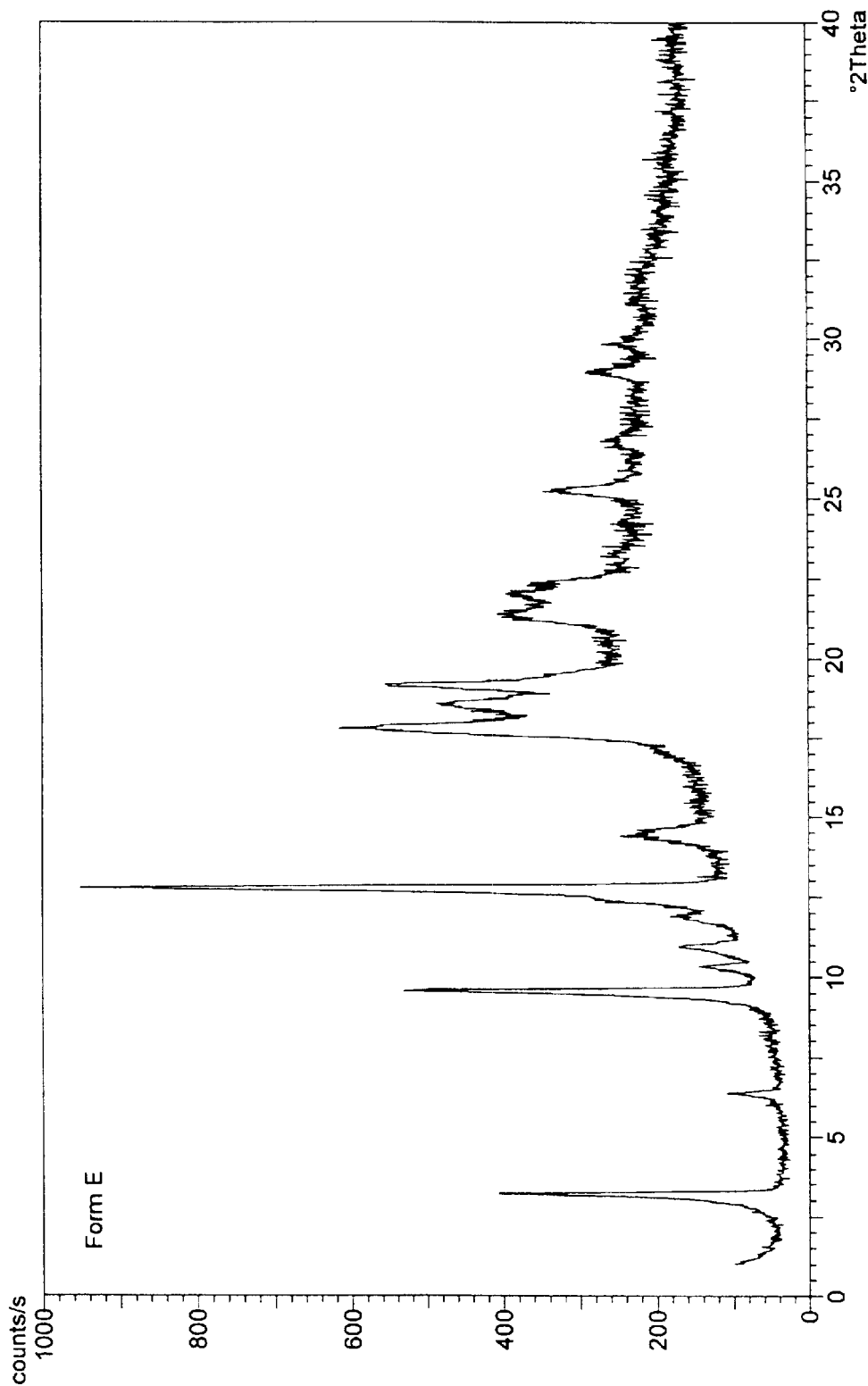
FIG. 4 is a characteristic X-ray powder diffraction pattern for Form E.
Figure 5:
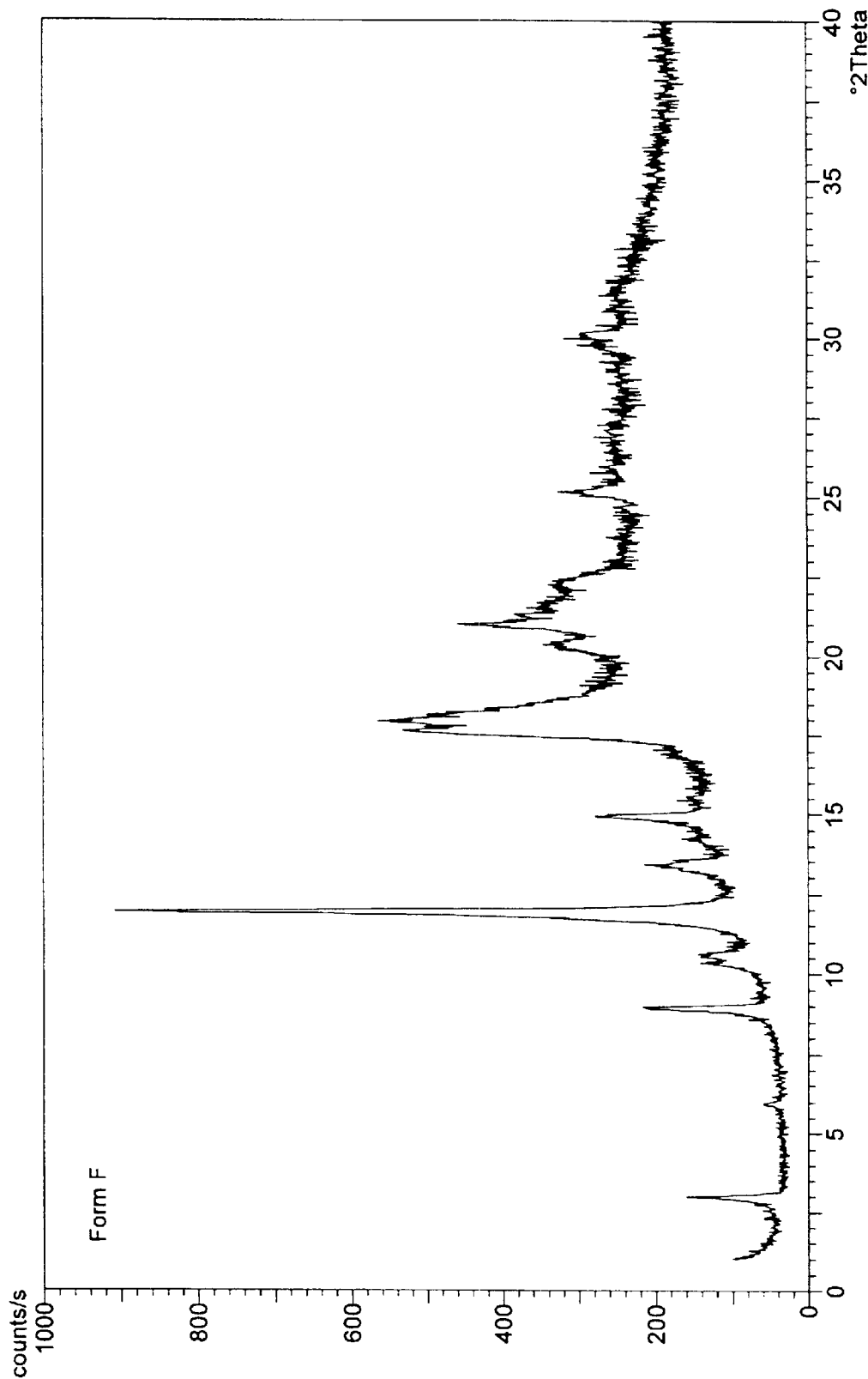
FIG. 5 is a characteristic X-ray powder diffraction pattern for Form F.
Figure 6:
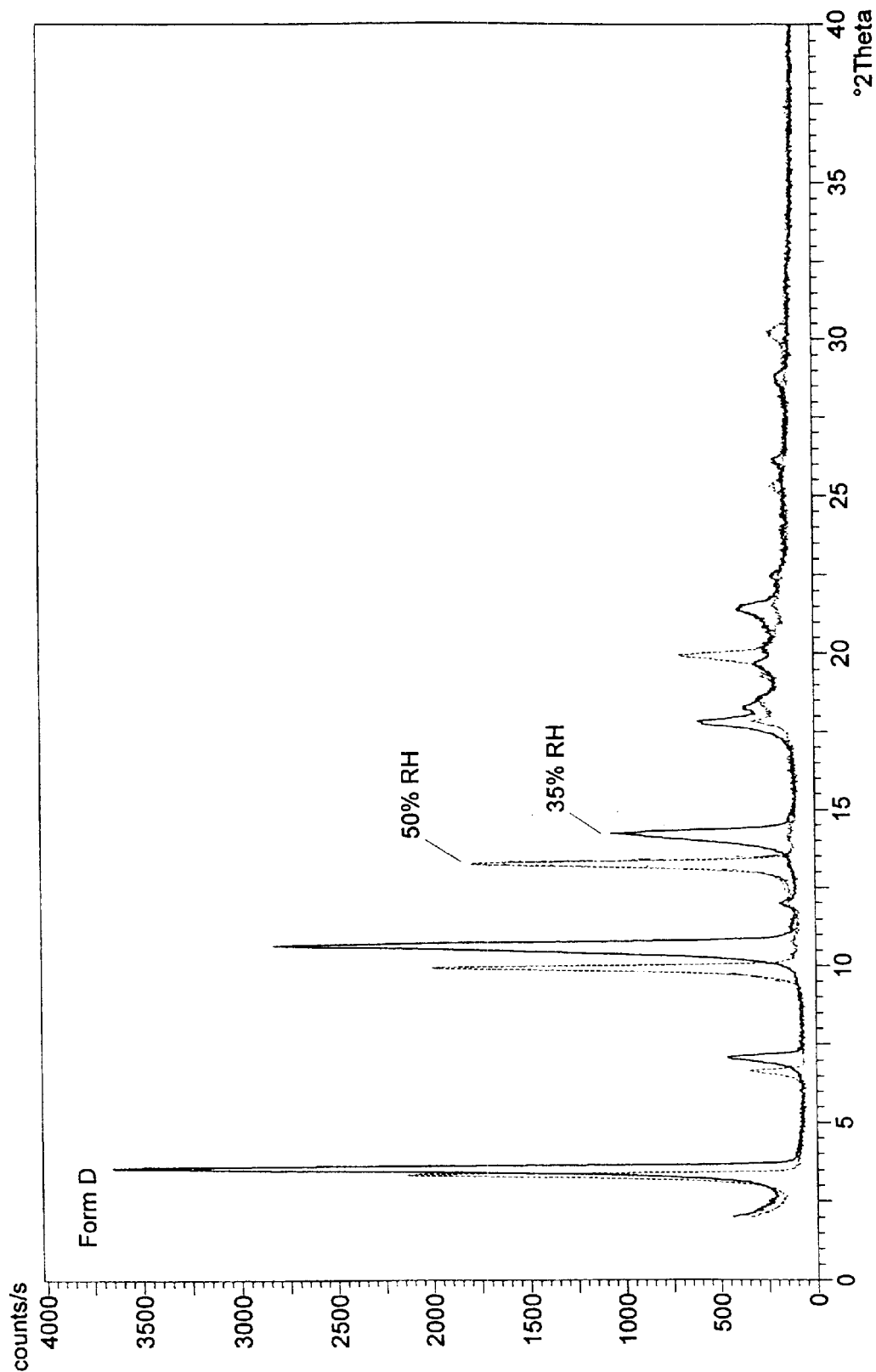
FIG. 6 shows the small deviations between characteristic X-ray powder diffraction patterns for Form D measured at 35 and 50% relative air humidity.

What is claimed is:
1. A crystalline polymorph of (±)-7-(3-(4-fluorophenyl)-1-(1-methylethyl)-1H-indol-2-yl)-3,5-dihydroxy-6-heptenoic acid monosodium salt which exhibits a characteristic X-ray powder diffraction pattern with characteristic peaks expressed in d-values (Å):

23.8 (vs), 11.8 (w), 7.8 (vs), 7.6 (vw), 7.4 (vw), 6.4 (vw), 6.1 (vw), 5.90 (w), 5.00 (vw), 4.88 (w), 4.73 (m), 4.56 (w), 4.40 (vw), 4.12 (vw), 4.03 (vw), 3.96 (vw), 3.50 (vw), 3.36 (vw), 2.93 (vw), wherein (vs)=very strong intensity; (m)=medium intensity; (w)=weak intensity; and (vw)=very weak intensity.

2. A pharmaceutical composition comprising an effective amount of a crystalline polymorphic form according to claim 1 and a pharmaceutically acceptable carrier.

3. A crystalline polymorph of (±)-7-(3-(4-fluorophenyl)-1-(1-methylethyl)-1H-indol-2-yl)-3,5-dihydroxy-6-heptenoic acid monosodium salt which exhibits a characteristic X-ray powder diffraction pattern with characteristic peaks expressed in d-values (Å):

24.6 (vs), 12.5 (w), 8.3 (vs), 7.4 (vw), 6.2 (m), 4.97 (w), 4.85 (vw), 4.52 (vw), 4.40 (vw), 4.14 (vw), 3.96 (vw), 3.41 (vw), 3.10 (vw), wherein (vs)=very strong intensity; (m)=medium intensity; (w)=weak intensity; and (vw)=very weak intensity.

4. A pharmaceutical composition comprising an effective amount of a crystalline polymorphic form according to claim 3, and a pharmaceutically acceptable carrier.

5. A process for the preparation of a crystalline polymorph according to claim 3, wherein Fluvastatin sodium is exposed to an atmosphere having a defined relative humidity.

6. A process according to claim 5 wherein the relative humidity is 30 to 50%.

7. A crystalline polymorph of (±)-7-(3-(4-fluorophenyl)-1-(1-methylethyl)-1H-indol-2-yl)-3,5-dihydroxy-6-heptenoic acid monosodium salt which can have small deviation in the characteristic peaks expressed in d-values (Å) in the X-ray powder diffraction pattern in the range of 24.6–26.2 (vs), 12.5–13.2 (w), 8.3–8.9 (vs) and 6.2–6.7 (m) depending on a relative humidity ranging from 35 to 50%, wherein (vs)=very strong intensity; (m)=medium intensity; (w)=weak intensity.

8. A pharmaceutical composition comprising an effective amount of a crystalline polymorphic form according to claim 7, and a pharmaceutically acceptable carrier.

9. A crystalline polymorph of (±)-7-(3-(4-fluorophenyl)-1-(1-methylethyl)-1H-indol-2-yl)-3,5-dihydroxy-6-heptenoic acid monosodium salt which exhibits a characteristic X-ray powder diffraction pattern with characteristic peaks expressed in d-values (Å):

27.6 (m), 13.9 (vw), 9.2 (m), 8.5 (vw), 8.1 (vw), 7.4 (vw), 6.9 (s), 6.1 (vw), 4.98 (m), 4.77 (m), 4.63 (m), 4.15 (w), 4.03 (w), 3.97 (vw), 3.52 (vw), 3.33 (vw), 3.08 (vw), 2.99 (vw), wherein (s)=strong intensity; (m)=medium intensity; (w)=weak intensity; and (vw)=very weak intensity.

10. A pharmaceutical composition comprising an effective amount of a crystalline polymorphic form according to claim 9, and a pharmaceutically acceptable carrier.

11. A crystalline polymorph of (±)-7-(3-(4-fluorophenyl)-1-(1-methylethyl)-1H-indol-2-yl)-3,5-dihydroxy-6-heptenoic acid monosodium salt which exhibits a characteristic X-ray powder diffraction pattern with characteristic peaks expressed in d-values (Å):

29.6 (w), 14.8 (vw), 9.9 (w), 8.6 (vw), 8.3 (vw), 7.4 (s), 6.6 (vw), 6.2 (vw), 5.93 (w), 5.03 (m), 4.94 (m), 4.35 (vw), 4.23 (w), 3.98 (vw), 3.54 (vw), 2.98 (vw), wherein (s)=strong intensity; (m)=medium intensity; (w)=weak intensity; and (vw)=very weak intensity.

12. A pharmaceutical composition comprising an effective amount of a crystalline polymorphic form according to claim 11, and a pharmaceutically acceptable carrier.

13. A process for the preparation of highly crystalline Fluvastatin sodium Form A, which comprises treating an aqueous solution of (±)-7-(3-(4-fluorophenyl)-1-(1-methylethyl)-1H-indol-2-yl)-3,5-dihydroxy-6-heptenoic acid monosodium salt in order to effect at least minimal precipitation of the compound, followed by freeze drying of the suspension or of the precipitated compound.

14. A pharmaceutical composition comprising an effective amount of a crystalline polymorphic form according to claim 13, and a pharmaceutically acceptable carrier.

15. A process according to claim 13, wherein the aqueous solution is cooled and subsequently the precipitated compound is freeze dried.

16. A process according to claim 15, wherein the aqueous solution is prepared at a temperature of 30 to 80° C. and is cooled to a temperature of 0 to 15° C. in order to effect precipitation of the compound.

17. A process according to claim 16, wherein seeding crystals of Form A are added.

* * * * *